(12) United States Patent
Kjaer et al.

(10) Patent No.: US 11,079,352 B2
(45) Date of Patent: Aug. 3, 2021

(54) MIXED IONOPHORE ION-SELECTIVE ELECTRODE FOR THE IMPROVED DETECTION OF UREA IN BLOOD

(71) Applicant: Radiometer Medical ApS, Brønshøj (DK)

(72) Inventors: Thomas Kjaer, Smoerum (DK); Lone Michelsen, Vanloese (DK); Poul Ravn Sorensen, Copenhagen K (DK); Hans Peter Blaabjerg Jakobsen, Roedoevre (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 201 days.

(21) Appl. No.: 16/062,211

(22) PCT Filed: Dec. 12, 2016

(86) PCT No.: PCT/EP2016/080607
§ 371 (c)(1),
(2) Date: Jun. 14, 2018

(87) PCT Pub. No.: WO2017/125208
PCT Pub. Date: Jul. 27, 2017

(65) Prior Publication Data
US 2018/0372671 A1 Dec. 27, 2018

(30) Foreign Application Priority Data
Dec. 18, 2015 (DK) .......................... PA 2015 00818

(51) Int. Cl.
*G01N 27/333* (2006.01)
*C12Q 1/58* (2006.01)
(Continued)

(52) U.S. Cl.
CPC .............. *G01N 27/333* (2013.01); *C12Q 1/58* (2013.01); *G01N 27/301* (2013.01); *G01N 27/3335* (2013.01); *G01N 27/4163* (2013.01)

(58) Field of Classification Search
CPC .............. G01N 27/333; G01N 27/3335; G01N 27/4163; G01N 27/301; G01N 33/49; C12Q 1/58
See application file for complete search history.

(56) References Cited

U.S. PATENT DOCUMENTS

| 4,762,594 A | 8/1988 | Guruswamy |
| 5,326,449 A * | 7/1994 | Cunningham ......... C12Q 1/002 204/403.09 |

(Continued)

FOREIGN PATENT DOCUMENTS

| CN | 1031425 A | 3/1989 |
| CN | 1216111 A | 5/1999 |

(Continued)

OTHER PUBLICATIONS

Bakker, Eric et al., "Ion-Selective Electrodes Based on Two Competitive Ionophores for Determining Effective Stability Constants of Ion—Carrier Complexes in Solvent Polymeric Membranes," Analytical Chemistry, vol. 70, No. 2, pp. 295-302 (1998).

(Continued)

*Primary Examiner* — J. Christopher Ball
(74) *Attorney, Agent, or Firm* — Finnegan, Henderson, Farabow, Garrett & Dunner, LLP

(57) ABSTRACT

The present application discloses improved multiple-use sensor arrays for determining the content of various species in samples of biological origin, in particular in the area of point-of-care (POC) testing for blood gases. The multiple-use sensor array is arranged in a measuring chamber, and the sensor array comprises two or more different ion-selective electrodes including a first ion-selective electrode (e.g. an (Continued)

ammonium-selective electrode being part of a urea sensor), wherein the first ion-selective electrode includes a membrane comprising a polymer and (a) a first ionophore (e.g. an ammonium-selective ionophore) and (b) at least one further ionophore (e.g. selected from a calcium-selective ionophore, a potassium-selective ionophore, and a sodium-selective ionophore), and wherein the first ionophore is not present in any ion-selective electrode in the sensor array other than in the first ion-selective electrode.

10 Claims, 4 Drawing Sheets

(51) Int. Cl.
  *G01N 27/416* (2006.01)
  *G01N 27/30* (2006.01)

(56) References Cited

U.S. PATENT DOCUMENTS

| | | | |
|---|---|---|---|
| 5,580,441 | A | 12/1996 | Amemiya et al. |
| 6,730,201 | B1 | 5/2004 | Kuhlman et al. |
| 2006/0060471 | A1 | 3/2006 | Murphy et al. |
| 2009/0170140 | A1* | 7/2009 | Collier .................. C12Q 1/58 435/12 |

FOREIGN PATENT DOCUMENTS

| | | |
|---|---|---|
| CN | 104086792 A | 10/2014 |
| CN | 104090014 A | 10/2014 |
| EP | 0 667 522 A2 | 8/1995 |
| JP | 1-502360 | 8/1989 |
| JP | H05-322843 | 12/1993 |
| JP | 2008-541103 | 11/2008 |
| JP | 2010-175275 | 8/2010 |
| WO | WO 2004/048960 A1 | 6/2004 |
| WO | WO 2009/094761 A1 | 8/2009 |
| WO | WO 2012/083371 A1 | 6/2012 |

OTHER PUBLICATIONS

Lee, K.S. et al., "Multiionophore-based solid-state potentiometric ion sensor as a cation detector for ion chromatography," Sensors and Actuators B, vol. 20, pp. 239-246 (1994).

International Search Report for International Application No. PCT/EP2016/080607, dated Jun. 19, 2017.

Written Opinion of the International Searching Authority of International Application No. PCT/EP2016/080607.

Mizutani, S. et al., "Development of Amperometric Ion Sensor Array for Multi-Ion Detection," IEEE Sensor Proceedings, pp. 1-4 (2015).

Qin, Y. et al., "Quantitative binding constraints of H+-selective chromionophores and anion ionophores in solvent polymeric sensing membranes," Talanta, vol. 58, p. 909-918 (2002).

* cited by examiner

MIXED IONOPHORE ION-SELECTIVE ELECTRODE FOR THE IMPROVED DETECTION OF UREA IN BLOOD

This application is a national stage filing under 35 U.S.C. § 371 of International Application No. PCT/EP2016/080607, filed on Dec. 12, 2016, which claims priority of Danish Patent Application No. PA 2015 00818, filed Dec. 18, 2015. The contents of these applications are each incorporated herein by reference.

FIELD OF THE INVENTION

The present invention relates to improved multiple-use sensor arrays for determining the content of various species in samples of biological origin. More specifically in the area of point-of-care (POC) testing for blood gases and in the evaluation of the so-called metabolic panel there is a need for a reliable, fast and precise determination of the concentration of urea in whole blood. Especially with respect to POC testing there is a need for the determination to occur at the highest possible speed, as the POC environment involves very ill patients that need fast evaluation of their condition. There is therefore specifically a need for urea sensors that can be deployed in a sensor cartridge format such as is now generally in use, whether single use or multiple use. The present invention relates to a fast multiple-use sensor array with short measuring time and short recovery time before the next measurement can be performed.

BACKGROUND OF THE INVENTION

In the operation of multiple-use sensor arrays arranged in a common measuring chamber, the sensors are collectively subjected to a rinse solution so as to make the sensors ready for a subsequent sample, as will be explained in greater detail next. This exposure of the sensors to the rinse solution constitutes the establishment of a so-called 1-point calibration of the status values of the sensors as the reference point for obtaining the differential signal value when the sensors are later subjected to a sample or a calibration solution. This principle applies to both electrical potential value measuring sensors (so-called potentiometric sensors) as well as to current measuring sensors (amperometric sensors). The term reference point should not be understood as indicating, that potentiometric sensors used in the described manner, do not require a reference electrode for completing the electrical measuring circuit. The reference point in the meaning described above is in fact nothing else but one of the necessary calibration points for calibrating a potentiometric sensor's slope and standard potential. This also explains why it is generally desirable to have primary ions of the potentiometric sensor present in all solutions used for calibrating the sensor. Primary ion should here be understood as the ion for which the sensor is most selective. It is also generally recognized, that potentiometric sensors also display signals when exposed to ions other than their primary ion. This is because the potentiometric sensor mechanism is based on molecular recognition and binding of the primary, and to a much lesser degree, also the secondary ions to the so-called ionophore molecule. In this framework the term primary ion means the ion that binds most specifically to the ionophore. The relationship between the activity of the primary ion, $a_I$, and the electrical potential registered against a suitable reference electrode, can be written as:

$$E = E^0 + (RT/nF) \cdot \ln[a_I]$$

This equation is sometimes also called the Nernst equation for the ion selective electrode. One may appreciate that when no primary ions are present in the solution, the term inside the logarithmic function is very small. Whereas of course the electrical potential in this case will not go to negative infinity, which would be physically meaningless, it nevertheless pinpoints the problems that arise from absence of primary ions. In practical experiments, when primary ions are absent, one does see poorly defined electrical potentials which may also be plagued by noise and/or drift. This has led to generalisations of the Nernst equation for ion selective electrodes, which can take the effects also of secondary ions into account. One well-known and often applied equation is the so-called Nicholskii-Eisenmann equation which adds terms inside the logarithmic function to account for secondary, interfering ions:

$$E = E^0 + S \log[a_I + \Sigma K_{I,J}(a_J)^{(zI/zJ)}]$$

where $a_I$ still is the activity of the primary ion, and $a_J$ is now the activity of any secondary ion.

Regarding the special case of requiring the presence also of ammonium ions in the rinse solutions of multiple-use sensor array, such as would be preferred for the reasons mentioned above, during the deployment of an ammonium-selective potentiometric sensor (ammonium-selective electrode) as the transduction element of an urea-to-ammonium converting biosensor, it has been found that the presence of ammonium ions is not desirable for many chemical reasons, as will be elaborated below. As can be appreciated this poses a dilemma, because for the reasons of obtaining a proper calibration of the sensor, it is greatly preferred to have the primary ion present.

As mentioned above, the presence of ammonium ions has been found to have impact on and even be detrimental to some other sensors. For instance in the case of a sensor for carbon dioxide it common to use a gas permeable membrane under which is placed a buffer solution containing bicarbonate ions. Most commonly a sodium bicarbonate solution in a concentration of between 10 mM and 100 mM is used. In the case that ammonium ions are present in the rinse solution, which also bathes the carbon dioxide sensor, ammonia, being a gas present in minute amounts in equilibrium with solutions containing ammonium ions, will diffuse into the inner sodium bicarbonate solution, and there be converted to ammonium ions. This will degrade the functioning of the carbon dioxide sensor.

Further, sensors for other ions, ion-selective electrodes (ISE), may be influenced in several ways, depending on the specific construction principle. Nowadays almost all POC multiple-use sensor-array based blood gas analysers deploy solid state ISEs. These typically have a mixed electronic/ionic conductor placed below an ion-selective membrane. For instance an electronically conducting polymer such as poly-octyl thiophene (PEDOT) or polyaniline (PANI) can be used. Other examples include oxides of transition elements, such as for example described in U.S. Pat. No. 6,805,781, which discloses an electrode device comprising an ion selective material, a solid state inner reference system of sodium vanadium bronze and a contact material. Again other examples include the use of a layer of silver chloride formed on top of a silver electrode. As said, should ammonia diffuse through the ion-selective membrane and reach the mixed conductor layer unexpected potential shifts or drift may be observed. This is due to the fact that ammonia, being a strong base, can interfere with equilibria poised at the conductor-to-membrane interface. Again the exact mechanism by which this can happens depends on the construction principle of the ISE.

Finally, amperometric sensors can also suffer from the presence of ammonium ions. This again is caused by the ability of ammonia to diffuse through polymeric membranes, also such as those used for amperometric sensors. As is well-known, many such sensors rely on the measurement of hydrogen peroxide generated from oxygen by enzymes that use oxygen as an electron acceptor. Often the measurement of hydrogen peroxide is accomplished by the use of a noble metal anode at which hydrogen peroxide is oxidized back to molecular oxygen. This process is accompanied by the generation of protons. This creates a feedback control mechanism with the anodic reactions on the noble metal electrode at which the reaction rates are pH dependent. Obviously, should ammonia diffuse to the surface of the noble metal electrode, as would surely be the case, this could impact the reactions occurring for hydrogen peroxide detection.

With respect to the presence of ammonia in rinse and calibration solutions this obviously poses an independent problem, as ammonia, it being a gas, can of course escape through polymeric materials whereby the concentrations and pH of the solution may change. This would be detrimental to the accuracy of the calibrations and introduce bias in the results.

It is further a problem, even if one should choose not to have ammonium ions in the rinse solution, that ammonium ions generated by the hydrolysis of urea, for instance in the biosensor layer of an urea sensor, determine the potential of an ammonium-selective electrode even at very low concentrations. This is because ammonium is the primary ion for the ammonium ISE itself. It therefore becomes very difficult to establish a baseline potential corresponding to the rinse level since the remaining traces of ammonium still are contributing to the potential generation. This will be explained in more detail below where the operational cycle of the rinse- and calibration solutions is explained.

Although explained above in the framework of an ammonium-selective electrode, whether for these alone or when used in urea sensors, the same will hold for other types of ion-selective electrodes present in multiple-use sensor arrays: The presence of the respective primary ions in the rinse solutions are required in order to establish a well-defined electrical potential upon rinse, however again such ions may cause harm to other electrodes. Although not exhaustively investigated, this could be the case for a number of anion- and cation-combinations, like lithium ions and magnesium ions.

To our knowledge, existing urea sensors for blood gas analyzers have not sought to solve this problem. Given a sufficient long cycle time of the analyzer, it would appear that the detrimental effects of not having ammonium ions in the rinse would not be very serious. The concentration of the remaining ammonium ions would fall to very low levels, given enough time and volume of rinse applied. The need for a very fast cycle time has however aggravated the problem.

WO 2004/048960 A1 discloses a multi-ionophore membrane electrode for used as a pseudo reference electrode for measurement of a plurality of ions like potassium, ammonium and sodium.

Lee et al. (1994) (K. S. Lee, J. H. Shin, M. J. Cha, G. S. Cha, M. Trojanowicz, D. Liu, H. D. Goldberg, R. W. Hower, R. B. Brown, "Multiionophore-Based Solid-State Potentiometric Ion Sensor as a Cation Detector for Ion Chromatography," Sensors and Actuators, B20, 1994, pp. 239-246) disclose multiion-selective membrane electrodes comprising e.g. valinomycin, nonactin and ETH 2120 as potassium, ammonium and sodium-selective ionophores.

Bakker and Pretsch (1998) (Bakker E, Pretsch E. Ion-selective electrodes based on two competitive ionophores for determining effective stability constants of ion-carrier complexes in solvent polymeric membranes. Anal Chem 1998; 70:295-302) disclose lithium-selective electrodes comprising a lithium-selective ionophore and an $H^+$-selective ionophore.

Qin and Bakker (2002) (Yu Qin, Eric Bakker. Quantitive binding constants of $H^+$-selective chromoionophores and anion ionophores in solvent polymeric sensing membranes. Talanta 58 (2002) 909-918) disclose the combination of anion ionophores and $H^+$-selective chromoionophores.

U.S. Pat. No. 4,762,594 relates to a method of generating an artificial reference (electrode) by incorporating a mixed ionophore electrode for compensating purposes. The US patent i.a. discloses a method for calibration measurement employing at least a first ion-specific sensor and a second ion-specific sensor where the first sensor is a combination electrode sensitive only to the first and second dissimilar chemical species and the second sensor is sensitive only to the second species.

U.S. Pat. No. 5,580,441 discloses an apparatus comprising a first ion-selective electrode for generating a potential in response to the measuring ion, and a second ion-selective electrode in response to the interfering ion.

U.S. Pat. No. 6,805,781 discloses an electrode device comprising an ion selective material, a solid state, inner reference system of sodium vanadium bronze and a contact material, where sodium may be reversibly intercalated in the bronze.

BRIEF DESCRIPTION OF THE INVENTION

One aspect of the invention relates to a multiple-use sensor array, cf. claim 1.

Another aspect of the invention relates to a method of operating the sensor array, cf. claim 5.

A third aspect of the invention relates to an ammonium-selective electrode, cf. claim 9.

A fourth aspect of the invention relates to a urea sensor, cf. claim 10.

A fifth aspect of the invention relates to the use of a rinse solution, cf. claim 11.

DETAILED DESCRIPTION OF THE INVENTION

Figure 1:
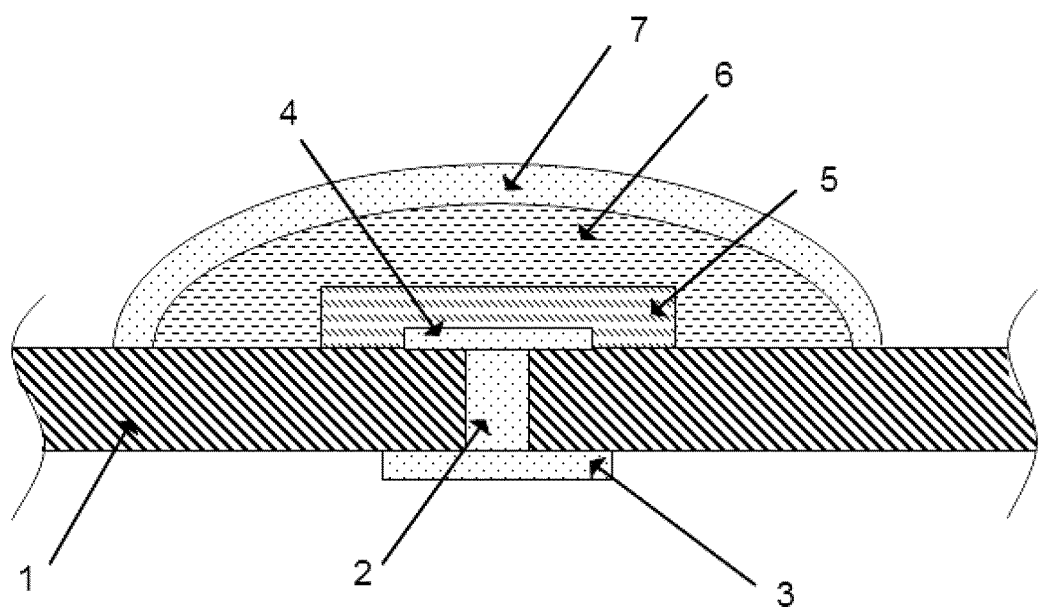
FIG. 1 illustrates the construction of a planar urea sensor with reference to the detailed description in Example 1.

The present invention relates to the field of multiple-use sensors mounted in sensor arrays for determining various species in samples of biological origin. Such species are both ionic species like $H^+$, $Na^+$, $K^+$, $Li^+$, $Mg^{2+}$, $Ca^{2+}$, $NH_4^+$, etc., as well as non-ionic species like urea, glucose, lactate, creatine, creatinine, etc. Urea is a special example because the detection thereof is indirect in the sense that in one commonly used and preferred type of urea sensors; urea is enzymatically degraded by urease to $NH_4^+$ which is then detected by an ion-selective electrode.

When used herein, the term "multiple-use sensor array" is intended to mean a sensor array that is mounted in an analyser over an extended period of time, typically many days, weeks or even months, and used for analysis several times. During the lifetime of the sensor array it is intermittently washed with rinse solution and flushed with calibration solutions containing different concentrations of the analytically interesting ions and molecules according to a calibration schedule. This allows determination of proper calibration functions.

The term "ionophore" here refers to molecules that are able to bind simple ions, the binding having certain distinguishing features: 1) the ionophore-ion complexes can easily dissociate into the empty ionophore and the ion, 2) the complex forms selectively, so that certain ionophores form complexes with certain ions, 3) the complex is mobile in the matrix, in which it is dissolved. Often ionophores are molecular cages or multi-dentate molecules that can form several bonds to the target ion. This enhances both specificity and bonding strength.

Examples of ionophores include valinomycin, 4-tert-butylcalix[4]-arene-tetracetic acid tetraethylester (commonly known as sodium ionophore X), nonactin, crown ethers, calixarenes, trialkylamines and phosphate esters.

Illustrative examples of ammonium-selective ionophores are nonactin (commonly known as ammonium ionophore I), which is a biologically derived substance. Other examples include synthetically derived ammonium ionophores, such as for instance described in WO 03/057649 or in Kim et al., "Thiazole-Containing Benzo-Crown Ethers: A New Class of Ammonium-Selective Ionophores" (Anal. Chem., 2000, 72 (19), pp 4683-4688).

Illustrative examples of potassium-selective ionophores are valinomycin, bis[(benzo-15-crown-4)-4'-yl methyl] pimelate (commonly known as potassium ionophore II) and 2-dodecyl-2-methyl-1,3-propanedi-yl-bis [N-(5'-nitro (benzo-15-crown-5) (commonly known as BME 44).

Illustrative examples of sodium-selective ionophores are 4-tert-butylcalix[4]arene-tetracetic acid tetraethylester (commonly known as sodium ionophore X), methoxyethyl-tetraester calix[4]arene (commonly known as METE), and derivatives of monensin.

An illustrative examples of lithium-selective ionophores are N,N'-diheptyl-N,N',5,5-tetramethyl-3,7-dioxanonoane-diamide (commonly known as lithium ionophore I).

An illustrative examples of magnesium-selective ionophores are N,N"-octamethylenebis (N'-heptyl-N'-methylmalonamide (commonly known as magnesium ionophore III or ETH 4030).

The Multiple-Use Sensor Array

As describe above, the present invention i.a. provides a multiple-use sensor array arranged in a measuring chamber, said sensor array comprising two or more different ion-selective electrodes including a first ion-selective electrode, said first ion-selective electrode including a membrane comprising (a) a first ionophore and (b) at least one further ionophore, said first ionophore not being present in any ion-selective electrode in the sensor array other than in the first ion-selective electrode.

The term "sensor array" is here intended to refer to a collection of two or more different sensors which are arranged in such a way that corresponding analytes of a fluid sample can be determined by the sensors substantially simultaneously.

The sensor array (i.e. an array of individual sensors) is arranged in a measuring chamber cell configuration so as to ensure that each sensor is exposed to the sample substantially simultaneously, as for instance described in U.S. Pat. No. 8,728,288 B2.

The sensor array comprises two or more different ion-selective electrodes. Preferably, the sensor array comprises at least three, such as at least four, or at least five, different ion-selective electrodes.

The first ion-selective electrode is typically selected from an ammonium-selective electrode.

The ion-selective electrodes in the sensor array other than the first ion-selective electrode typically include at least a sodium-selective electrode and a potassium-selective electrode.

In some interesting embodiment, ion-selective electrodes in the sensor array other than the first ion-selective electrode typically include at least a sodium-selective electrode, a potassium-selective electrode, and a calcium-selective electrode.

In some interesting embodiments, the sensor array also includes sensors for other non-ionic species, such as one or more selected from glucose, lactate, creatine, and creatinine.

Moreover, the sensor array also typically includes a reference electrode.

EMBODIMENTS

In one interesting embodiment of the sensor array, the first ion-selective electrode is selected from an ammonium-selective electrode, a lithium-selective electrode, and a magnesium-selective electrode. In particular, the first ion-selective electrode is an ammonium-selective electrode.

In important variants hereof, the ammonium-selective electrode forms a part of a urea sensor, which according to this embodiment comprises an ammonium-selective electrode with an enzyme layer thereon. Said enzyme layer comprises a urease enzyme capable of converting urea into ammonium, which is finally is detected by the underlying ammonium-selective electrode.

One important variant of the ammonium-selective electrode (e.g. as being a part of a urea sensor) is the one where the membrane thereof comprises a polymer and two ionophores being (a) an ammonium-selective ionophore and (b) a further ion-selective ionophore selected from a calcium-selective ionophore, a potassium-selective ionophore, and a sodium-selective ionophore.

Further features of the ammonium-selective electrode are those described further below under the heading "Ammonium-selective electrode".

Further features of the urea sensor are those described further below under the heading "Urea sensor".

The Method of Operating the Sensor Array

The invention also provides a method of operating the sensor array defined hereinabove, the method comprising the steps of:
i. in sequence contacting the sensor array with one or more rinse solutions and optionally one or more calibration solutions, each of said rinse solutions being substantially devoid of the ion for which said first ionophore is selective;
ii. subsequently contacting the sensor array with a sample of biological origin.

When used herein, e.g. for the rinse solutions, the term "substantially devoid of" is intended to mean that the content of the respective constituent(s) is less than $1.0 \times 10^{-6}$ M. Preferably, the content of the respective constituent(s) is less than $10 \times 10^{-6}$ M, such as $1.0 \times 10^{-9}$ M.

When used herein, the term "sample of biological origin" is intended to mean liquid samples taken from physiological fluids. Illustrative examples hereof are those like blood (e.g. whole blood, blood plasma, blood serum, blood fractions, etc.), urine, dialysate and pleura.

In regular use, when in the idle state and ready for performing a measurement, the sensor array is always bathed in the rinse solution. Typically for optimal performance the composition of the rinse solution is chosen to be near the composition of the sample of biological origin, when no deviating conditions apply, such as for example hypoxia (too low oxygen concentration), hypernatremia (too high sodium concentration) or any other non-standard condition, which could apply if the donating patient were ill. When the sample, e.g. a whole blood sample, is introduced, the remaining rinse solution is quickly flushed away from the sensor arrays, preferably by introducing a small volume of gas (e.g. pure air or oxygen), and then the sample is moved in front of the sensor array. Now the sample may either have higher or lower concentrations of any of the substances that should be measured. One can envisage the sensor signals as then either moving upwards away from the rinse level or downwards if the levels are below normal. This explains also why the rinse solution is termed a 1-point calibration, because in the sample measurement situation the differential value between the rinse and the sample forms the primary result that enters into the ensuing calculations, for instance as explained by the use of the Nernst calibration function. Having obtained this differential value, the sample is now moved away and the measuring chamber is flushed with rinse solution to restore the sensor array for the next measurement.

In the cases where the first ion-selective electrode of the sensor array is an ammonium-selective electrode, and wherein such an ammonium-selective electrode is part of a urea sensor, the rinse solution is preferably devoid of ammonium ions as well as urea.

Further, to the way the sensor arrays typically are operated, it can be appreciated, that switching between rinse solution and sample has consequences for the sensor signals. For an ion-selective electrode some ions may have been absorbed into the outermost layer of the sensor membrane, requiring some time to diffuse back to the rinse solution. Particularly for the ammonium-selective electrode, when used to determine ammonium ions generated in the enzyme layer of a urea sensor, a special situation arises. When urea is converted to ammonium ions and ammonia by the action of urease, ammonia in particular can be absorbed into the membrane of the ammonium-selective electrode. Upon switching the sample with rinse after the measurement, some ammonia may linger in the membrane and only leave slowly. When it leaves it is immediately converted back to ammonium ions which then impact the signals as if ammonium would have been added to the rinse solution. The effect of the presence of a first and a second ionophore as suggested here is to lower the detrimental effects of this lingering ammonium release.

The steps i. and ii., mentioned above, are repeated in as many cycles as is necessary to perform the measurements and restorations of the idle condition.

The method of the invention thus obviously renders it possible to utilize much shorter measuring cycle times, because detrimental effects from lingering ions or molecules, that require time to diffuse out of the sensor is reduced. Typically, the sampling cycle time when using the multiple-use sensor array described herein is 5-120 seconds, e.g. 10-90 second, such as 15-60 seconds, or even 15-30 seconds.

In some preferred embodiments of the method of the invention, the first ion-selective electrode (and other ion-selective electrodes not being the first electrode) is as described herein, in particular as described under the heading "The multiple-use sensor array"-"Embodiments".

A multiple-use sensor array arranged in a measuring chamber, said sensor array comprising two or more different ion-selective electrodes including a first ion-selective electrode and a second ion-selective electrode, said first ion-selective electrode including a membrane comprising (a) a first ionophore and (b) at least a second ionophore, said second ion-selective electrode including a membrane comprising the second ionophore, said first ionophore not being present in any ion-selective electrode in the sensor array other than in the first ion-selective electrode.

Now in regular operation the first ion-selective electrode including (a) the first ionophore and (b) a second ionophore (and possible, but not preferably, further ionophores), and the second ion-selective electrode including the second ionophore (and not the first ionophore) is used as follows: The presence of two ionophores in the first ion-selective electrode has rendered it collectively sensitive to the primary ions of both the first ionophore and the second ionophore. Surprisingly the responses very closely follow the Nernst equation including the Nicholski-Eisenmann term for allowing the second ion to be taken into account. The second ion-selective electrode on the contrary responds only to the primary ion of the second ionophore and renders an independent determination of the concentration of that ion possible through regular use of the calibration function of that ion-selective electrode. Finally, the concentration of the primary ion of the first ion-selective electrode can be obtained by subtracting the concentration of the second ion, now known as just described. Because the selectivity of the first ion-selective electrode towards the second ion has purposely been elevated by the addition of the second ionophore this allows the determination of the concentration of the first ion by subtraction.

Ion-Selective Electrodes

The ion-selective electrode is typically a planar electrode device which is provided on a substrate of an electrically insulating material supporting an electrode layer of an electrically conductive material and on which the ion-selective membrane of the ion-selective electrode is arranged.

The substrate may be presented in any shape desired, and it typically also constitute a support for other ion-selective electrodes (including the second ion-selective electrode) and sensors (e.g. enzyme sensors) thereby constituting a common substrate for a sensor array.

The support can be made of any suitable electrically insulating material. However, it must be able to resist the conditions under which the sensor array is prepared and used. The substrate usually comprises a ceramic or polymeric material. Ceramic substrates have the advantage that they are thermally, mechanically and chemically stable. If ceramic substrates are used in combination with polymeric membranes, it may be necessary to use an adhesive material so that the membrane adheres to the adhesive material and the adhesive material adheres to the substrate. An example is disclosed in U.S. Pat. No. 5,844,200. Aluminium oxide and fosterite are ceramic materials which are suitable as substrates. Polymeric substrates are more economic to use and may result in a better adhesion between polymeric membranes and the substrate, than in the case of a ceramic substrate. Among polymeric materials which may be suitable as supports can be mentioned polyvinyl chloride, polyester, polyimide (Kapton®), poly(methylmethacrylate) and polystyrene.

The electrically conductive material typically is made of or comprises one or more precious metals, such as gold, palladium, platinum, rhodium or iridium, preferably gold or platinum, or mixtures thereof. Other suitable electrically conductive material are graphite or iron, nickel or stainless steel. The electrically conductive material can be mixed with another component, such as a binder system having an advantageous effect on the properties of the electrically conductive material, both in connection with the preparation and the use of ion-selective electrode. The electrically conductive material may further comprise a bronze material, such as a $Na_{0.33}V_2O_5$ bronze, e.g. of the type discloses in U.S. Pat. No. 6,805,781. Such a bronze material is typically covering an electrically conductive material of a precious metal.

The ion-selective electrode further includes a membrane comprising one or more ionophores (as specified further above), a polymer, optionally a plasticizer and optionally a lipophilic salt. The membrane is covering the electrically conductive material. Suitable polymeric materials for the membrane are, e.g., polyvinyl chloride, polymethacrylates, polyacrylates, silicones, polyesters or polyurethane or mixtures hereof, such as carboxylated polyvinyl chloride and polyurethane with varying amount of polyethylene glycol and polypropylene glycol. Among suitable plasticizers can be mentioned dioctyl-adipate, 2-nitrophenyl octylether, dioctyl sebacate, dioctyl phthalate. Illustrative examples of lipophilic salts are potassium tetrakis(4-chlorophenyl)borate, tetradodecylammonium tetrakis(4-chlorophenyl)borate and potassium tetrakis[3,5-bis (trifluoromethyl)phenyl]borate.

The ion-selective electrode is typically prepared by methods suitable for miniaturisation, such as by thick-film printing, drop casting, spray-coating or spin-coating. A preferred embodiment of the ion-selective electrode is a planar, miniaturised electrode prepared at least in part by thick-film printing. Advantageous properties for such ion-selective electrodes are that they only require very small sample volumes, and that the method of preparation is suitable for mass production of ion-selective electrodes as well as sensor arrays. If desired, only the electrically conductive material is applied by thick-film printing, after which the ion-selective material membrane is applied.

Ammonium-Selective Electrode

The invention further provides an ammonium-selective electrode including a membrane, wherein the membrane comprises a polymer and two ionophores being (a) an ammonium-selective ionophore and (b) a further ion-selective ionophore selected from a calcium-selective ionophore, a potassium-selective ionophore, and a sodium-selective ionophore.

The ammonium-selective electrode comprises a substrate of an electrically insulating material supporting an electrode layer of an electrically conductive material. The substrate and electrode layer has an ammonium-selective ionophore containing polymer membrane disposed thereon. The principles for the construction of the ammonium-selective electrode may be as described in Example 1.

In one important variant, the ammonium-selective ionophore is nonactin, and the further ion-selective ionophore is a potassium-selective ionophore, in particular valinomycin.

In important variants hereof, the ammonium-selective electrode is part of a urea sensor (see further below under the section "Urea sensor").

Lithium-Selective Electrode

The invention further provides a lithium-selective electrode including a membrane, wherein the membrane comprises a polymer and two ionophores being (a) a lithium-selective ionophore and (b) a further ion-selective ionophore selected from a calcium-selective ionophore, a potassium-selective ionophore, and a sodium-selective ionophore.

The construction and preferences for the lithium-selective electrode essentially follows that generally described for the ion-selective electrode above, but with the use of a lithium-selective ionophore, such as N,N'-diheptyl-N,N',5,5-tetramethyl-3,7-dioxanonoanediamide (commonly known as lithium ionophore I).

Magnesium-Selective Electrode

The invention further provides a magnesium-selective electrode including a membrane, wherein the membrane comprises a polymer and two ionophores being (a) a magnesium-selective ionophore and (b) a further ion-selective ionophore selected from a calcium-selective ionophore, a potassium-selective ionophore, and a sodium-selective ionophore.

The construction and preferences for the magnesium-selective electrode essentially follows that generally described for the ion-selective electrode above, but with the use of a magnesium-selective ionophore, such as N,N"-octamethylenebis(N'-heptyl-N'-methylmalonamide (commonly known as magnesium ionophore III or ETH 4030).

Urea Sensor

The invention further provides a urea sensor comprising an ammonium-selective electrode as define hereinabove (see under the section "Ammonium-selective electrode").

Hence, the urea sensor comprises:
(i) an ammonium-selective electrode including a membrane, wherein the membrane comprises a polymer and two ionophores being (a) an ammonium-selective ionophore and (b) a further ion-selective ionophore selected from a calcium-selective ionophore, a potassium-selective ionophore, and a sodium-selective ionophore; and
(ii) an enzyme layer covering the electrode, said enzyme layer comprising a polymer and urease; and
(iii) optionally an outer layer covering the enzyme layer.

The enzyme layer typically contains urease and a polymer, e.g. carboxylated polyvinyl chloride or polyurethane with varying amount of polyethylene glycol and polypropylene glycol.

The optional outer layer contains polyurethane with varying amount of polyethylene glycol and polypropylene glycol.

The principles for the construction of the urea sensor may be as described in Example 1.

Use of a Rinse Solution

Unlike conventional multiple-use sensor arrays comprising an ammonium-selective electrode (possibly as a part of a urea sensor), wherein the rinse solutions applied subsequent to sampling include measurable amounts of ammonium (and/or urea), the inclusion of (an)other ionophore(s) in the electrode membrane of the ammonium-selective electrodes of the invention renders it possible to avoid the use of ammonium as well as urea in the rinse solutions.

Hence, the invention provides the use of a rinse solution for a multiple-use sensor array comprising two or more different ion-selective electrodes including an ammonium-selective electrode, said rinse solution being substantially devoid of urea and ammonium ions.

EXAMPLES

Example 1

Construction of an Urea Sensor Having Included an Ammonium-Selective Electrode The ammonium-selective electrode device according to the invention shown in FIG. 1 is of a type which can be characterised as a planar, miniaturised electrode device, as described in U.S. Pat. No. 6,805,781. The electrode device shown is provided on a polymeric support 1, of PVC. A hole with a diameter of 0.01 mm through the support is filled with platinum paste 2, as a contact material by thru-hole printing. This filling mediates electrical contact between a lower contact surface 3, of gold paste on the one side of the support and an upper contact surface 4, of gold paste on the other side of the support. The upper contact surface 4, of platinum paste is in contact with the reference system 5, of sodium vanadium bronze paste. The platinum paste is completely covered by the bronze paste. Above the reference system an ion selective PVC-membrane 6, including the first ionophore and the at least second ionophore, is applied completely covering the reference system 5. Above the PVC-membrane is an enzyme layer 7, of urease. The diameter of the electrode device is about 1.5 mm. During use of the electrode device, the lower contact surface 3, is connected with usual measuring equipment, e.g. via an outer electric conductor.

Example 2

Ammonium-Selective Electrodes for Testing

Ammonium-selective electrodes were prepared according to the description in Example 1 except for the absence of an enzyme layer and an outer layer.

The ammonium-selective membrane 6 was prepared from a solution in cyclohexanone of PVC, a plasticizer such as dioctyl sebacate, a lipophilic salt such as potassium tetra(p-chloro-phenyl borate) and the ammonium-selective ionophore nonactin. Valinomycin was not added in this solution (A). With valinomycin in the solution, this substance was added to the cyclohexanone solutions in the amounts of, given as mole percent of the nonactin present, (B) 2.6 mol % valinomycin, (C) 5.2 mol % valinomycin, (D) 13 mol % valinomycin, and (E) 26 mol % valinomycin.

Figure 2:
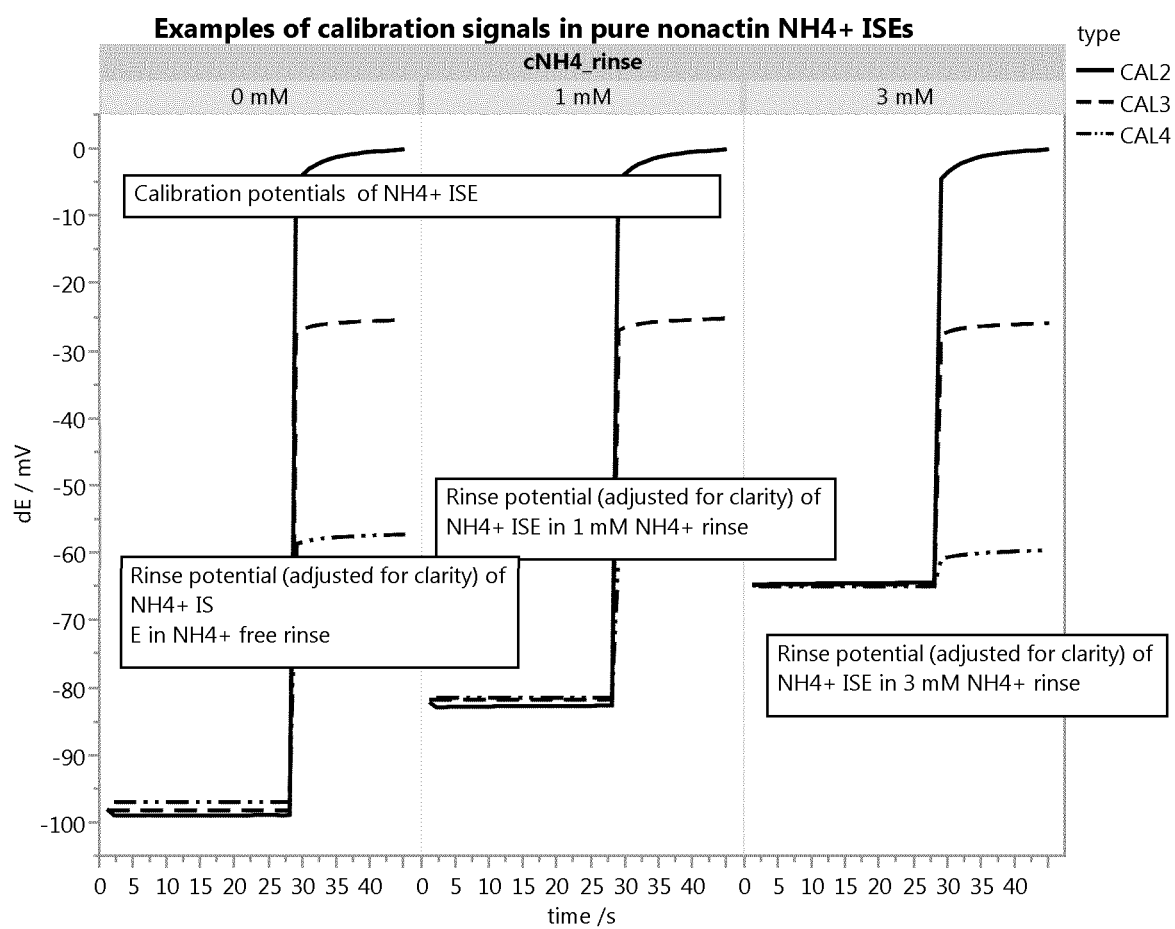
FIG. 2 and FIG. 3 show the responses of an ammonium-selective electrode without and with valinomycin added to the ion-selective membrane, cf. Example 2.

The responses of the ammonium-selective electrode upon rinse and calibration without valinomycin (A) included in the membrane are shown in FIG. 2. The effect of presence/absence of ammonium ions is seen in that different levels of the potentials registered when rinse is measured. When ammonium ions are present in the rinse solution (1 mM and 3 mM $NH_4^+$, respectively), the sensors all reach the same levels.

Figure 3:
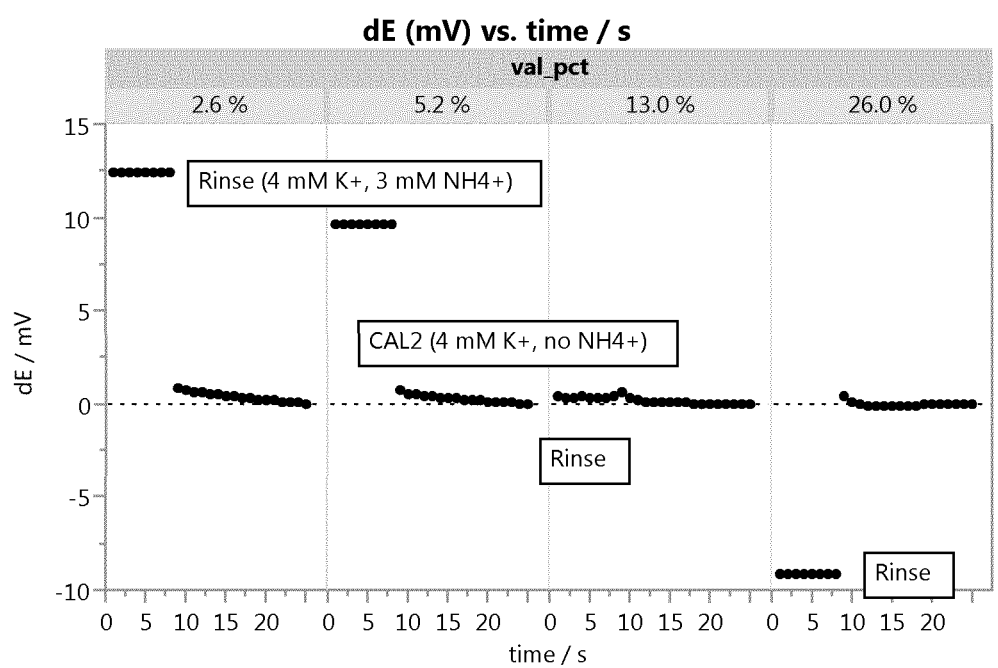

The responses of the ammonium-selective electrode upon rinse and calibration with valinomycin (B)-(E) included in the membrane are shown in FIG. 3. From left to right the concentration of valinomycin in the membrane increases. The electrodes were investigated in modified analyzers that could hold several electrodes simultaneously so as to investigate the responses under identical conditions, while only the electrodes themselves were different. The electrodes were all calibrated in the following manner: first the electrodes were subjected to a calibration solution without any ammonium ions present. This established a baseline potential. Then the rinse solution was flushed in front of the sensors providing a reading on an ammonium ion comprising solution. The rinse contained 4 mM of $K^+$ and 3 mM of $NH_4^+$ whereas the calibration solutions also contained 4 mM of $K^+$ but no $NH_4^+$. According to the levels of valinomycin in the membranes, the electrodes now reacted differently depending on the valinomycin concentration. For clarity the potentials have all been shifted to show a common value of the potentials of the rinse solution. In reality, both the rinse potential and the value obtained on the ammonium ion containing calibration solutions were different between the studied electrodes.

Example 3

Operation of a Multiple-Use Sensor Array

Figure 4:
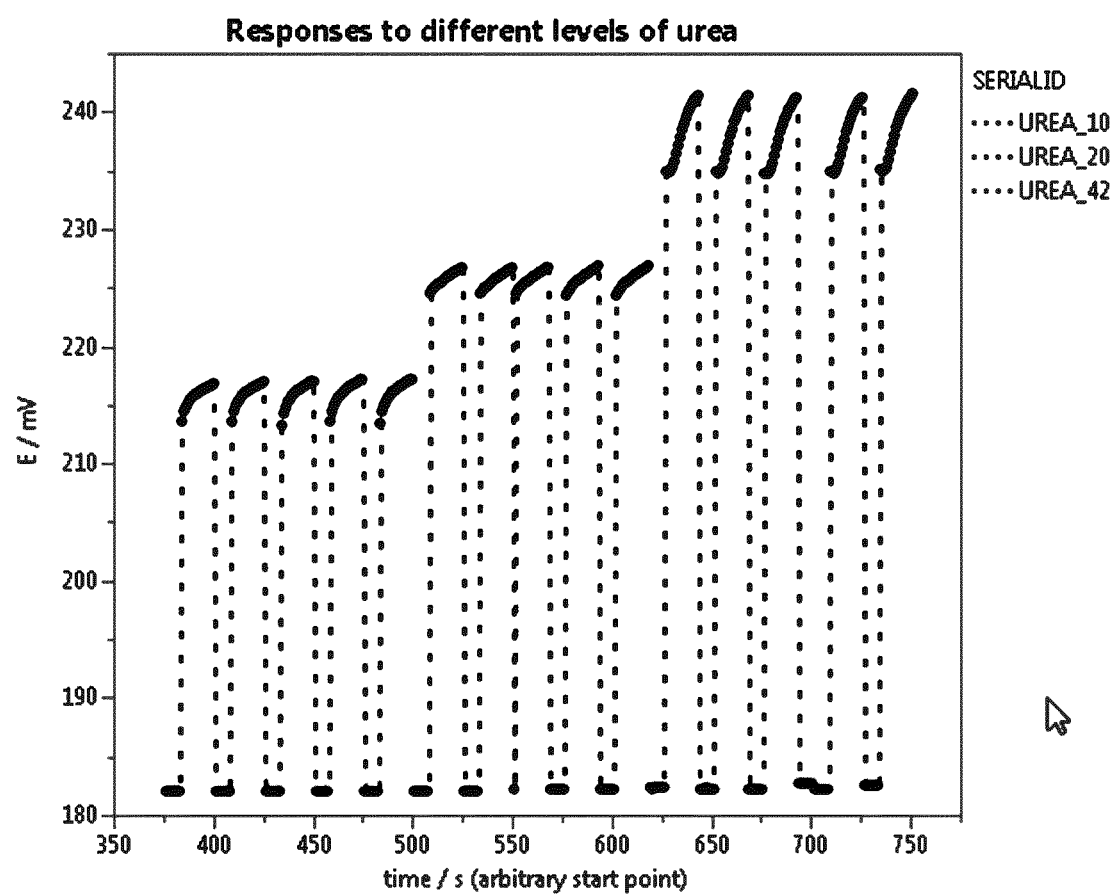
FIG. 4 relates to the operation of the multiple-use sensor array and shows the electrode responses of a urea sensor in a multiuse sensor array.

FIG. 4 relates to the operation of the multiple-use sensor array and shows electrode responses of a urea sensor in a multiuse sensor array. The urea sensors of the multi-use sensor array were produced as described in Example 1, with a valinomycin content of 30 mol %. The sensors were further covered with a urease containing biosensor membrane to make it sensitive towards urea. The sensor array was mounted in a modified blood gas analyzer which held one sensor array, providing the sensing capability, and one solution pack, containing all the necessary solutions to perform calibrations and measurements. Further, the analyzer comprises a set of software programs which controls the flow of solutions. The urea sensors are calibrated on urea containing solutions whereas the rinse solution is devoid of this substance and also of ammonium ions. Upon being exposed to the rinse, the electrodes establish a potential measured against a suitable reference electrodes, integrated in the multi-use sensor array. Several readings of the rinse potential are stored in a computer memory. The calibration solutions (the signals from these are not shown) and samples are introduced sequentially and the respective potential values are obtained. Signals for three different levels of urea concentrations (10 mM, 20 mM and 42 mM of urea) are shown in FIG. 4. For each sample, the concentration of urea is calculated by considering the registered and stored rinse potential values and the potential values obtained from the sample. The differential signal is obtained by subtraction and a set of algorithms are used to obtain the urea concentration.

General Remarks

Although the present description and claims occasionally refer to a ionophore, a sensor, an electrode, etc., it should be understood that the products and methods defined herein may comprise one, two or more types of the individual constituents or elements. In the embodiments wherein two or more different constituents are present, the total amount of the respective constituents should correspond to the amount defined herein for the individual constituent.

The "(s)" in the expressions: compound(s), ionophore(s), electrode(s), etc. indicates that one, two or more types of the individual constituents or elements may be present. On the other hand, when the expression "one" is used, only one (1) of the respective constituent or element is present.

Throughout the specification the word "comprise", or variations such as "comprising" or "comprises", will be understood to imply the inclusion of a stated element, integer or step, or groups of elements, integers or steps, but not the exclusion of any other element, integer or step, or groups of elements, integers or steps.

The invention claimed is:

1. A method of operating a multiple-use sensor array, said method comprising:

(i) providing a multiple-use sensor array arranged in a measuring chamber, said sensor array comprising two or more different ion-selective electrodes including a first ion-selective electrode and a second ion-selective electrode, said first ion-selective electrode including a membrane comprising (a) a first ionophore and (b) at least one second ionophore, said second ion-selective electrode including a membrane comprising at least one of the at least one second ionophores, said first ionophore not being present in any ion-selective electrode in the sensor array other than in the first ion-selective electrode;

(ii) in sequence contacting the sensor array with one or more rinse solutions and optionally one or more calibration solutions, each of said rinse solutions being substantially devoid of the ion for which said first ionophore is selective;

(iii) subsequently contacting the sensor array with a sample of biological origin.

2. The method according to claim 1, wherein the first ion-selective electrode of the sensor array is an ammonium-selective electrode.

3. The method according to claim 2, wherein the membrane of said ammonium-selective electrode comprises a polymer and two ionophores being (a) an ammonium-selective ionophore and (b) a further ion-selective ionophore selected from a calcium-selective ionophore, a potassium-selective ionophore, and a sodium-selective ionophore.

4. The method according to claim 2, wherein the first ion-selective electrode is an ammonium-selective electrode that is part of a urea sensor.

5. The method according to claim 4, wherein the membrane of said ammonium-selective electrode comprises a polymer and two ionophores being (a) an ammonium-selective ionophore and (b) a further ion-selective ionophore selected from a calcium-selective ionophore, a potassium-selective ionophore, and a sodium-selective ionophore.

6. The method according to claim 1, wherein (ii) and (iii) are repeated in several cycles.

7. The method according to claim 6, wherein a sampling cycle time is the time for performing (ii) and (iii), and wherein the sampling cycle time is 15-60 seconds.

8. The method according to claim 1, wherein the first ion-selective electrode is selected from an ammonium-selective electrode, a lithium-selective electrode, and a magnesium-selective electrode.

9. The method according to claim 1, wherein one or more of the one or more rinse solutions is substantially devoid of urea and ammonium ions.

10. A urea sensor comprising:

an ammonium-selective electrode comprising a membrane, said membrane comprising a polymer and two ionophores, wherein the two ionophores are an ammonium-selective ionophore and a potassium-selective ionophore;

an enzyme layer covering the electrode, said enzyme layer comprising a polymer and urease; and an outer layer covering the enzyme layer.

* * * * *